United States Patent [19]
Uematsu et al.

[11] Patent Number: 5,538,849
[45] Date of Patent: Jul. 23, 1996

[54] APPARATUS FOR AUTOMATED ASSAY OF DNA PROBE AND METHOD FOR ASSAYING NUCLEIC ACID IN SAMPLE

[75] Inventors: Hiroaki Uematsu; Makoto Tsuruoka; Takashi Nakajima; Ken-ichi Chikanari; Misao Yoshimoto; Hiromichi Kobata, all of Ohtsu, Japan

[73] Assignee: Toyo Boseki Kabushiki Kaisha, Osaka, Japan

[21] Appl. No.: 174,308

[22] Filed: Dec. 29, 1993

[30] Foreign Application Priority Data

Dec. 29, 1992 [JP] Japan ................... 4-360557
Feb. 5, 1993 [JP] Japan ................... 5-018925
Sep. 17, 1993 [JP] Japan ................... 5-231431

[51] Int. Cl.$^6$ ............ C12Q 1/68; G01N 21/00; G01N 35/00; C12N 15/00
[52] U.S. Cl. ............ 435/6; 435/287.2; 422/55; 422/62; 422/63; 422/82.05; 422/100; 422/104; 436/43; 436/48; 436/49; 436/94; 536/23.1; 536/24.3
[58] Field of Search ............ 435/6, 291; 422/82.05, 422/55, 62, 63, 93, 100, 104, 173, 174; 436/43, 48, 49, 94, 805, 807, 808; 536/23.1, 24.3; 935/76, 77, 85, 86, 87

[56] References Cited

U.S. PATENT DOCUMENTS 5,358,691  10/1994  Clark et al. ............... 422/64

OTHER PUBLICATIONS

Keller et al., *American Clinical Laboratory*, Nov. 1988, pp. 10–15.

*Primary Examiner*—W. Gary Jones
*Assistant Examiner*—Bradley L. Sisson
*Attorney, Agent, or Firm*—Leydig, Voit & Mayer

[57] ABSTRACT

An apparatus is presented for an automated assay of a DNA probe, which is performed by hybridizing a nucleic acid in a sample with a DNA probe marked with an enzyme and optically measuring a change that occurs in the substrate by catalysis of the enzyme which is bound with the DNA probe. The DNA probe hybridizes with the nucleic acid in the sample to assay the nucleic acid in the sample. Comprising (A) a sample-reagent unit, (B) a sample-reagent dispense unit, (C) a reaction vessel transport unit, (D) a hybridization unit, (E) a B/F separation unit, and (F) a light measurement unit; also presented is a method for assaying a nucleic acid in a sample by the apparatus of the present invention. According to the measurement apparatus of the present invention, a continuous and highly precise measurement is attainable. In particular, the light-shielding structure of the light measurement unit exhibits high levels of light-shielding effect and contributes to efficient light measurement and prevention of degradation of light receiving elements.

12 Claims, 14 Drawing Sheets

APPARATUS FOR AUTOMATED ASSAY OF DNA PROBE AND METHOD FOR ASSAYING NUCLEIC ACID IN SAMPLE

TECHNICAL FIELD OF THE INVENTION

The present invention relates to an apparatus for an automated assay of a DNA probe by a nucleic acid hybridization method, comprising hybridizing a nucleic acid in a sample with a DNA probe marked with an enzyme, thereby inducing an optically-measurable change in a substrate by catalysis of the enzyme, and measuring said change in an automated, continuous and precise manner to assay the nucleic acid in the sample; and to a method for assaying the nucleic acid in the sample by the said apparatus.

BACKGROUND OF THE INVENTION

The nucleic acid hybridization method has been widely used in a variety of fields as a method having high specificity based on the complimentarity of nucleic acids.

The hybridization method includes, for example, dot hybridization wherein a nucleic acid is directly immobilized on a membrane, colony hybridization wherein a bacterium is incubated on a membrane, Southern blot technique wherein a nucleic acid is fractionated by electrophoresis as it is or upon cleavage with a restriction enzyme and transferred to a nitrocellulose membrane etc. for hybridization, and in site hybridization method done on a glass slide as described herein below.

An attempt has been made to immobilize a nucleic acid onto a microplate, beads, latex particles etc. rather than onto conventional membranes.

In addition, a DNA probe which is used for the above-exemplified hybridization varies depending on the marker (label) to be used including, for example, a probe reagent using a radioactive substance as a marker, a probe reagent using an enzyme as a marker, a probe reagent using a chemical fluorescent substance as a marker, a probe reagent using a chemical luminescent substance as a marker and so on.

Tests using a DNA probe for the diagnosis of infectious diseases and genetic disorders have been drawing much attention in recent years. In this connection, kits for diagnosis of infectious diseases using a DNA prove have been marketed.

In such a test, a step in the DNA probe assay particularly requires handling of a trace amount of a sample with precision for a long time tedious and time-consuming work to do. What is more, the assay is susceptible to an error due to inconsistent control of hybridization temperatures by an individual operator and contamination due to a very low concentration of a sample. Motivated thereby, there is a great demand in the market for a system enabling an automated mechanical assay of a DNA probe, which is still left to be satisfied.

Accordingly, an object of the present invention is to provide an apparatus for an automated assay suitable for a DNA probe hybridization method, comprising measurement of an optically-measurable change in a substrate, which is caused by catalysis of an enzyme used as a marker.

Another object of the present invention is to provide a device for measuring light, which comprises a simple light-shielding structure permitting effective shielding of light from outside during measurement of the target light, and an apparatus for an automated assay comprising this light measurement device.

Still another object of the present invention is to provide a device for measuring light with high measurement precision, which permits prevention of outside light and stray light from invading into a light receiving part of an emitted light detection part when a light measurement is or is not underway, and an apparatus for an automated assay comprising this light measurement device.

A further object of the present invention is to provide a method for assaying a nucleic acid in a sample, which permits efficient and continuous measurement of a multitude of samples.

SUMMARY OF THE INVENTION

As a result of an intensive study of the inventors, it has now been found that the following combination can result in the achievement of the aforementioned objects of the present invention. That is, the combination of a specific arrangement of the devices necessary for hydridization, B/F separation and light measurement on a circulation line; and use of a device having an arm part freely movable to the directions of the X-Y-Z axes for dispensing a sample and a reagent, as well as for transporting reaction vessels.

Accordingly, the present invention provides an apparatus for an automated assay of a DNA probe which is performed by hybridizing a nucleic acid in a sample with a DNA probe marked with an enzyme and optically measuring a change that occurred in a substrate by catalysis of the enzyme which is bound with the DNA probe hybridized with the nucleic acid in the sample to assay the nucleic acid in the sample, comprising at least:

A—a sample-reagent unit,
B—a sample-reagent dispense unit,
C—a reaction vessel transport unit,
D—a hybridization unit,
E—a B/F separation unit, and
F—a light measurement unit, wherein the sample-reagent unit A comprises a sample tube containing a sample, a reaction vessel in which a captured DNA probe has been immobilized, a reagent pack containing a DNA probe marked with an enzyme and an enzyme substrate, a reagent cassette integrally composed of a mixing tank and a holder in which a reaction vessel is movably held, an alkaline denaturant reservoir and a washing solution reservoir set at predetermined positions;

the sample-reagent dispensing unit B comprises an arm part freely movable to the directions of the X-Y-Z axes, a mechanism to move said arm part, a tip nozzle set in the arm part, a tip to be set at the nozzle, a tip rack carrying the tip and placed at a predetermined position, the tip being set at the head portion of the tip nozzle by moving said arm, thereby enabling suction and injection of the sample in the sample tube and the reagent in the reagent pack;

the reaction vessel transport unit C comprises a vessel holding device formed on the arm part;

a mechanism to move said arm part and a mechanism to transport the reaction vessel carried by the vessel holding device to a stock part of a measurement rack;

the hybridization unit D comprises a circulation device to circulate the measurement rack carrying reaction vessels from the stock part through an incubator part composed of a heating device and a shaking device to the stock part, and a device for sequentially sucking a sample to be made single-stranded from a mixing tank in the reagent cassette with the tip nozzle equipped with a tip of the sample-reagent dispense unit and a DNA probe marked with an enzyme from the reagent pack, and respectively dispensing them to a reaction vessel to be transported from the stock part to the incubator part;

the B/F separation unit E comprises a discharge nozzle and a washing solution nozzle to be set in the arm part movable to the X-Y-Z axes, a device for sucking the content of the reaction vessel (after hybridization) with said discharge nozzle to discharge same to the outside and sucking a washing solution from the washing solution reservoir with said washing solution nozzle to inject same into a reaction vessel, and a circulation mechanism for the above-mentioned hybridization unit; and the light measurement unit F comprises a mechanism for sucking an enzyme substrate from the reagent pack in the reagent cassette with a tip nozzle equipped with a tip of the sample-reagent dispense unit and injecting same into a reaction vessel after B/F separation, a circulation mechanism for the above-mentioned hybridization unit and a light measurement device for measuring an optically measurable change in the reaction vessel.

The method for assaying a nucleic acid in a sample by the aforedescribed apparatus for an automated assay of DNA probe comprises the following four steps:

(a) a sample denaturing step wherein a sample in a sample tube and an alkaline denaturant from an alkaline denaturant reservoir are sequentially sucked with a tip nozzle equipped with a tip of a sample-reagent dispense unit, simultaneously dispensed to a mixing tank in a reagent cassette and mixed to make the nucleic acid in the sample single-stranded;

(b) a hybridization step wherein a reaction vessel in which a capturing probe has been immobilized is transported from the reagent cassette into a holder in a measurement rack in a stock part of a hybridization unit by a reaction vessel transport unit, the single-stranded nucleic acid, which was sucked from the mixing tank with a tip nozzle equipped with a tip of the sample-reagent dispense unit, is dispensed to said reaction vessel, a DNA probe marked with an enzyme, which was sucked from a reagent pack in the reagent cassette with a tip nozzle equipped with a tip, is dispensed to said reaction vessel, and the measurement rack is passed to an incubator part by a circulation mechanism to apply heating and shaking to allow hybridization in said reaction vessel;

(c) a B/F separation step wherein the content of the reaction vessel (after the hybridization) is sucked with a discharge nozzle of the sample-reagent dispense unit and discharged, a washing solution is sucked from a washing solution reservoir with a washing solution nozzle of said dispense unit and injected in said reaction vessel, the measurement rack is passed to the incubator part by the circulation mechanism to apply heating and shaking to allow B/F separation in said reaction vessel, and the washing solution is sucked with a discharge nozzle from the reaction vessel after the B/F separation and discharged; and (d) a light measurement step wherein an enzyme substrate is sucked from the reagent pack in the reagent cassette with a tip nozzle equipped with a tip of the sample-reagent dispense unit and injected into the reaction vessel, the measurement rack is passed to the incubator part by the circulation mechanism to apply heating, the measurement rack is transported to a light measurement part by the circulation device to perform measurement of a light change occurred in the reaction vessel with the use of a light measurement device.

According to the apparatus of the aforementioned structure, an automated assay of a nucleic acid in a sample becomes attainable, with the effect that measurement operators are released from a tedious and time-consuming work and an error due to inconsistent control of hybridization temperatures by an individual operator and contamination due to a very low concentration of a sample can be avoided.

According to the method using the apparatus of the aforementioned structure, a change in light produced by a sample in a reaction vessel can be automatically and continuously measured with high precision. Therefore, a nucleic acid in a sample can be assayed with high efficiency and dependability.

DETAILED DESCRIPTION OF THE INVENTION

The apparatus for an automated assay of a DNA probe of the present invention is explained in more detail by referring to the attached drawings showing the embodiments of the present invention.

Figure 1:
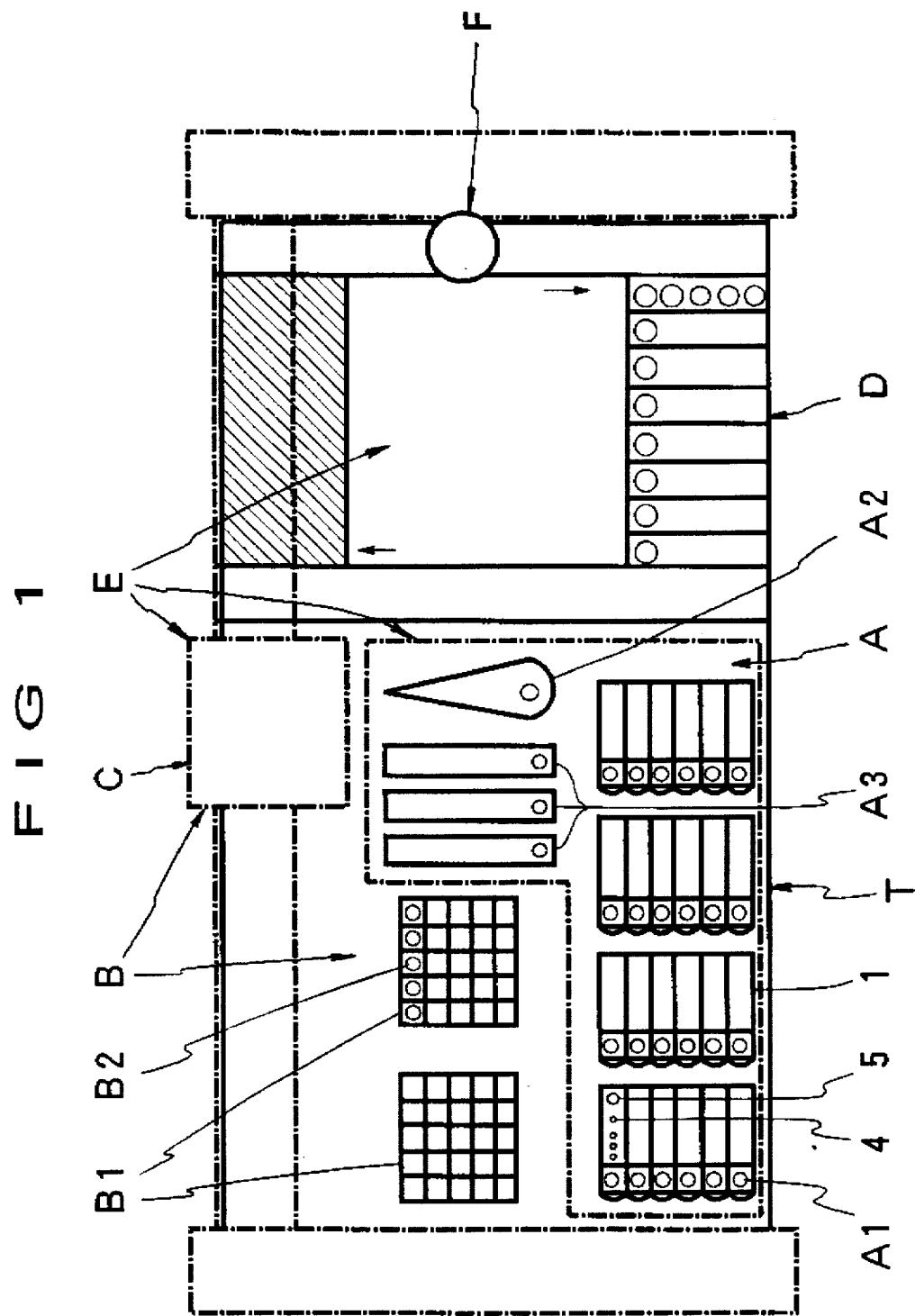
FIG. 1 is a schematic diagram showing one embodiment of the internal structure of a measurement part of an apparatus for an automated assay of a DNA probe of the present invention.

FIG. 1 is a schematic diagram showing an internal structure of a measurement part of an apparatus for an automated assay of a DNA probe, which is used for the treatment system for hybridization using a DNA probe. In the Figure, T is a measurement part comprising a sample-reagent unit A, a sample-reagent dispense unit B, a reaction vessel transport unit C, a hybridization unit D, a B/F separation unit E and a light measurement unit F.

While the above-mentioned apparatus can be controlled from semi-automatic to full-automatic by various methods, it is preferable that a fully-automated assay of a nucleic acid in a sample should be performed by controlling the operation of each of the above units according to a computer program.

The sample-reagent unit A comprises a sample tube A1 containing a sample, a reagent cassette 1, a reservoir A2 for reserving an alkaline solution to denature a sample into single-stranded nucleic acid and a washing solution reservoir A3, all of which are set at selected positions in the measurement part (T).

Figure 2:
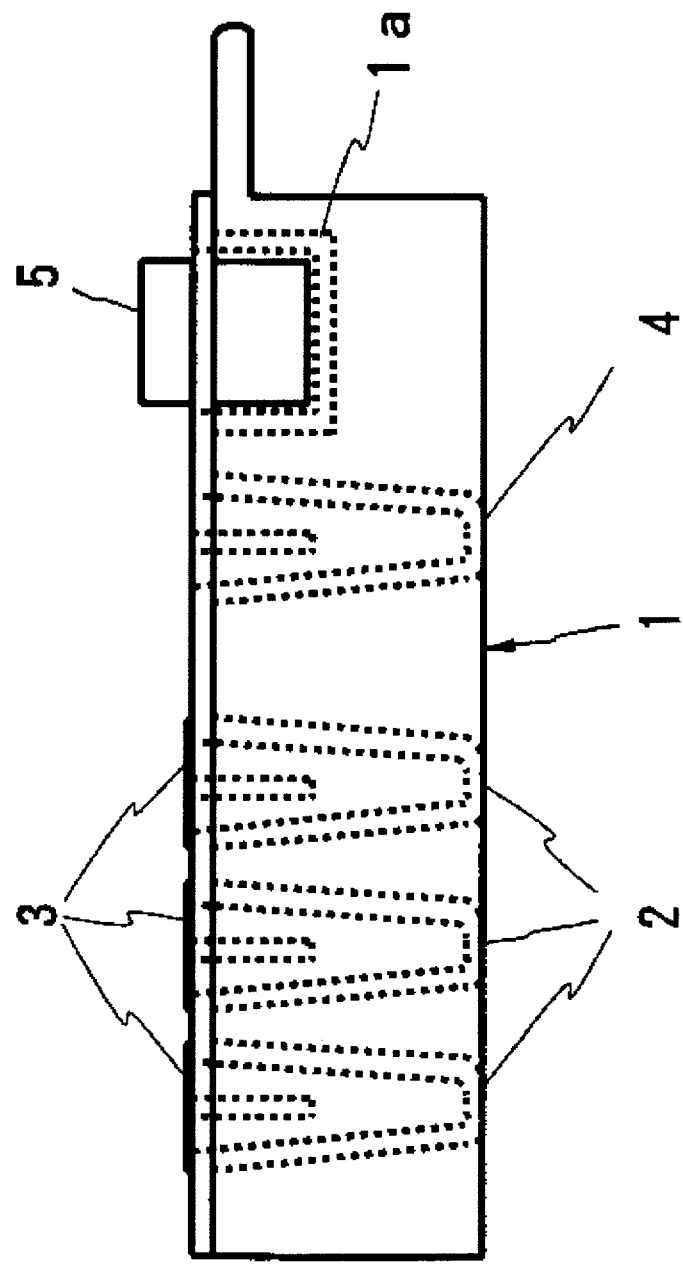
FIG. 2 is a side view of one embodiment of the structure of a reagent cassette.

The reagent cassette has a structure as shown in FIG. 2 (side view), wherein 1 is a reagent cassette integrally composed of a reagent pack part 2 containing a plurality of reagent packs, a mixing tank 4 and a holder 1a holding a reaction vessel 5.

In said reagent pack part 2, reagent parts necessary for each measurement item, such as a DNA probe marked with an enzyme, buffer, substrate and so on, are stored with its opening usually sealed with a laminate seal 3.

To the mixing tank 4, a sample and an alkaline denaturant are dispensed. By thoroughly mixing the two, a double-stranded nucleic acid in a sample is denatured into a single-stranded one.

The holder 1a holds a reaction vessel 5 carrying a bound DNA probe immobilized on the internal surface thereof, in a movable fashion.

The sample-reagent dispense unit B comprises an arm part 11 freely movable to the directions of the X-Y-Z axes, which is installed above the measurement part of said apparatus for an automated assay of a DNA probe, a mechanism to move the arm part, a tip nozzle 7 to be provided in the arm part, a tip B2 to be set at the tip nozzle and a tip rack B1 provided at the selected position in the measurement part T for the purpose of holding tips B2 before use, the tip B2 being set at the head portion of the top nozzle by moving said arm, thereby enabling suction and injection of the sample in the sample tube A1 and the reagent into the reagent pack 2.

Figure 3:
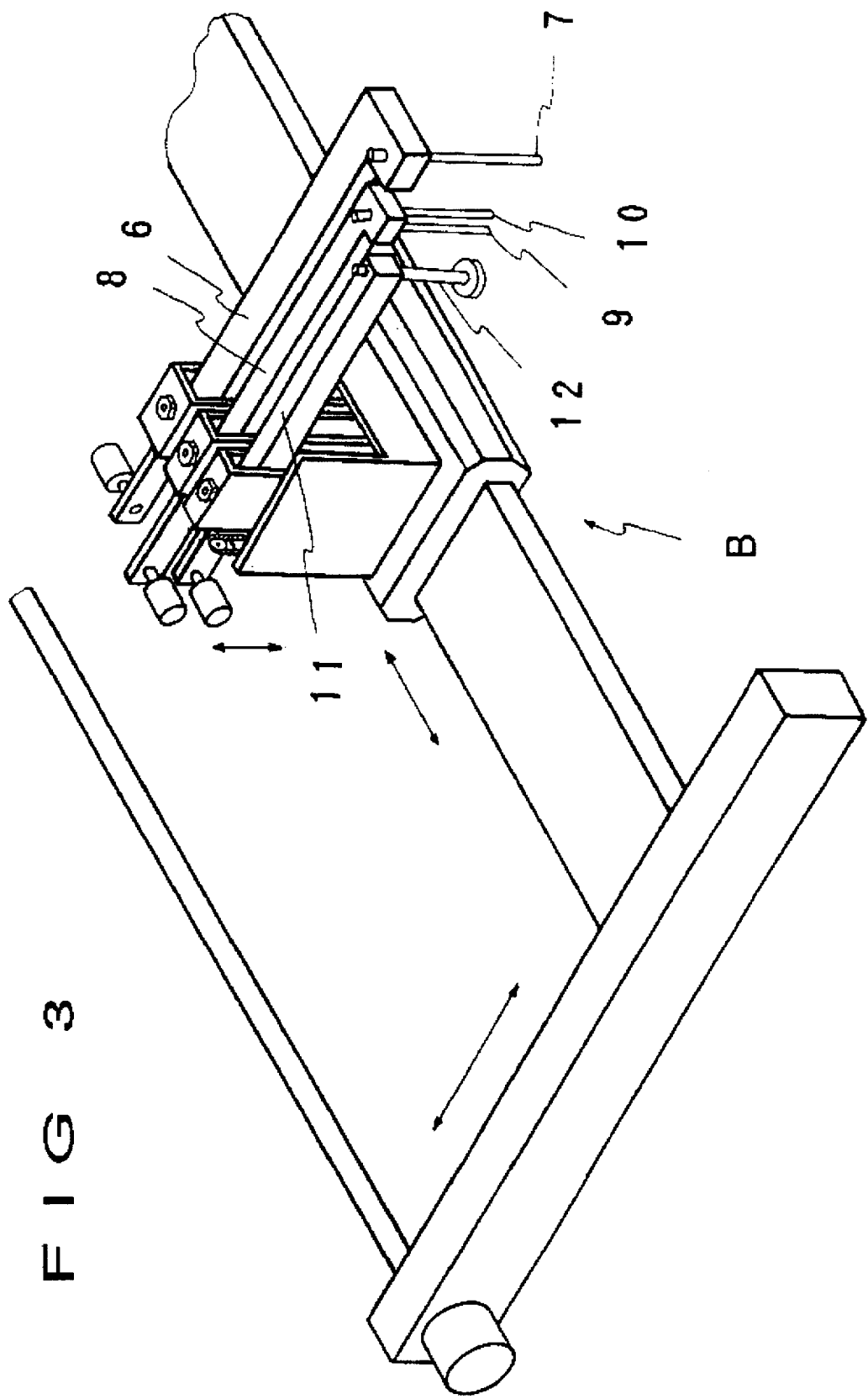
FIG. 3 is a perspective view of one embodiment of the structure of an arm part with a nozzle of a dispense unit.

FIG. 3 is a partial perspective view of the arm part of the aforementioned dispense unit, wherein B is a dispense unit movable in the directions of the X-Y-Z axes, the arm part 6 has a tip nozzle 7 at which a tip is set, the tip nozzle 7 being coupled to a piper (not shown) for sucking and dispensing specific amounts of sample and reagent.

An arm part 8 disposed in a parallel relation to the arm part 6 has a discharge nozzle 9 for the B/F separation unit, to discharge samples and reagents in reaction vessels, and a washing nozzle 10 for injecting a washing solution, the discharge nozzle 9 being coupled to a discharge purpose pump (not shown) and the washing nozzle 10 being coupled to a pipet (not shown) for sucking and dispensing specific amounts of washing solution.

The reaction vessel transport unit C accompanies a vessel holding device 12 for holding a reaction vessel by an arm part 11 movable in the directions of the X-Y-Z axes.

The vessel holding device 12 may be a conventional one based on vacuum sucking or chucking.

The arm part of said dispense unit may be moved in the direction of the X, Y or Z axis by a known mechanism.

The hybridization unit D comprises a circulation mechanism for circulating a measurement rack 16 carrying reaction vessels from a stock part 14 through an incubator part 15, having a heating device and a shaking device, to a stock part and a device to sequentially suck a sample to be made single-stranded from a mixing tank in a reagent cassette and a reagent DNA probe marked with an enzyme from the reagent pack using a tip nozzle equipped with a tip of the sample-reagent dispense unit, and to dispense them to the reaction vessel to be transported from the stock part to the incubator part.

Figure 4:
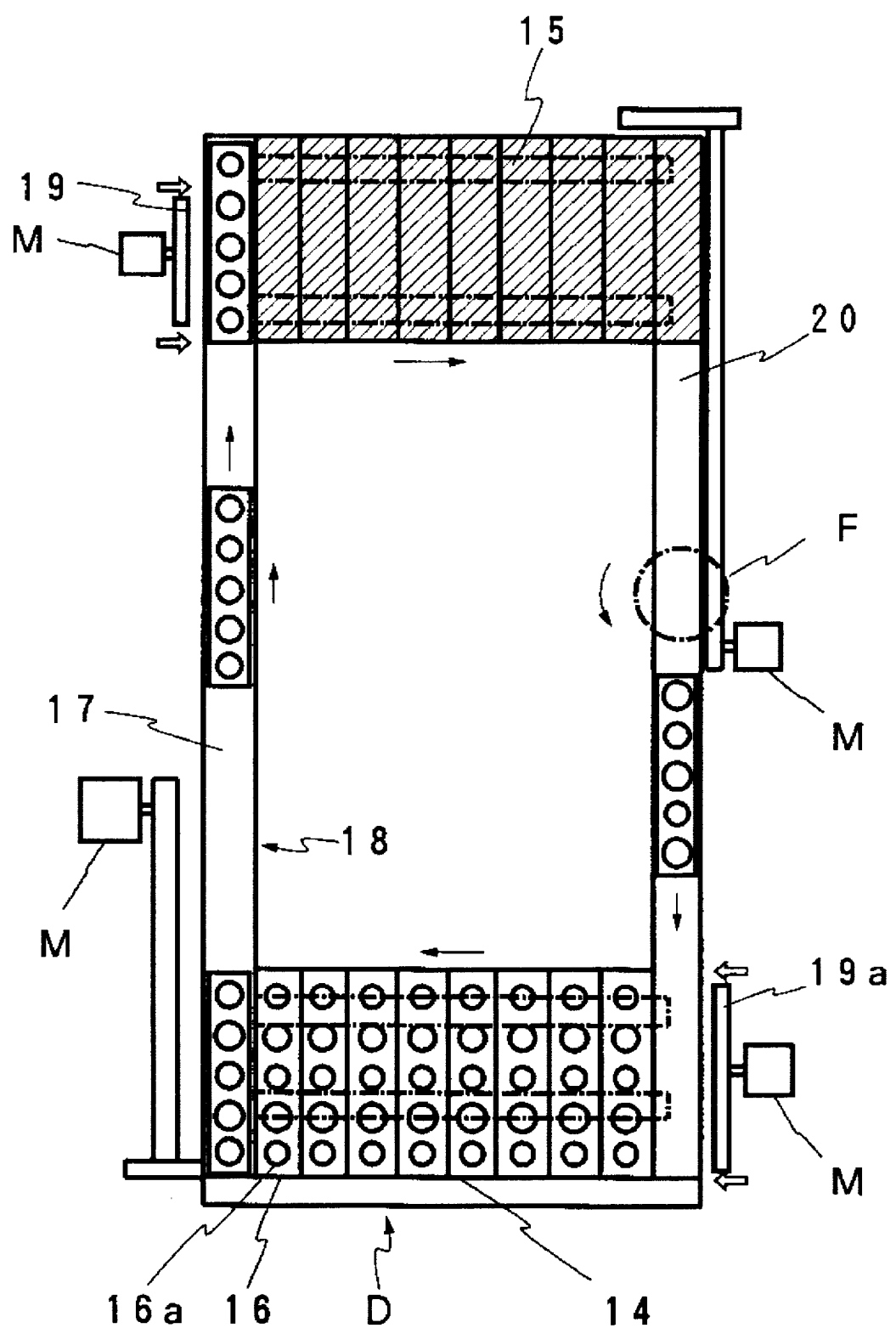
FIG. 4 is a schematic drawing of one embodiment of the structure of a hybridization unit.

FIG. 4 is a schematic drawing showing the structure of the hybridization unit D. As shown in the figure, the hybridization unit comprises a circulation mechanism consisting of a stock part 14 for stocking a measurement rack 16 having holders 16a capable of holding a plurality of reaction vessels 5, a dispense line 17 by which the single-stranded sample and a reagent are dispensed to a reaction vessel 5 which has been housed in the measurement rack 16 at a predetermined position 18 while transporting the measurement rack 16 to the incubator part 15, the incubator part 15 to apply heating and shaking as necessary to allow hybridization in said reaction vessel, and a transport line 20 for transporting the measurement rack 16 after hybridization to the stock part 14.

As described in the above, the hybridization unit is basically a circulation mechanism. In this embodiment, 8 sets of the measurement rack 16 each capable of carrying five reaction vessels 5 such as microplates are stocked respectively in said stock part 14 and the incubator part 15. Upon activation of a motor M connected to the dispense line 17, the measurement rack positioned at the exit of the stock part 14 is transported to the entrance of the incubator part 15 one by one and transferred to the inside of the incubator part 15 by a pusher 19, whereby an empty measurement rack at the exit of the incubator part 15 is pushed out onto the transport line 20. Upon activation of a motor M connected to the transport line 20, the empty rack is transported to the entrance of the stock part 14 and transferred to the inside of the stock part 14 by a pusher 19a, whereby a measurement rack at the exit of the stock part 14 is pushed out onto the dispense line 17.

Whereafter, cycles of the above-described circulation of measurement racks are repeated in such a manner that eight measurement racks always reside at the stock part 14 and the incubator part 15.

Figure 5:
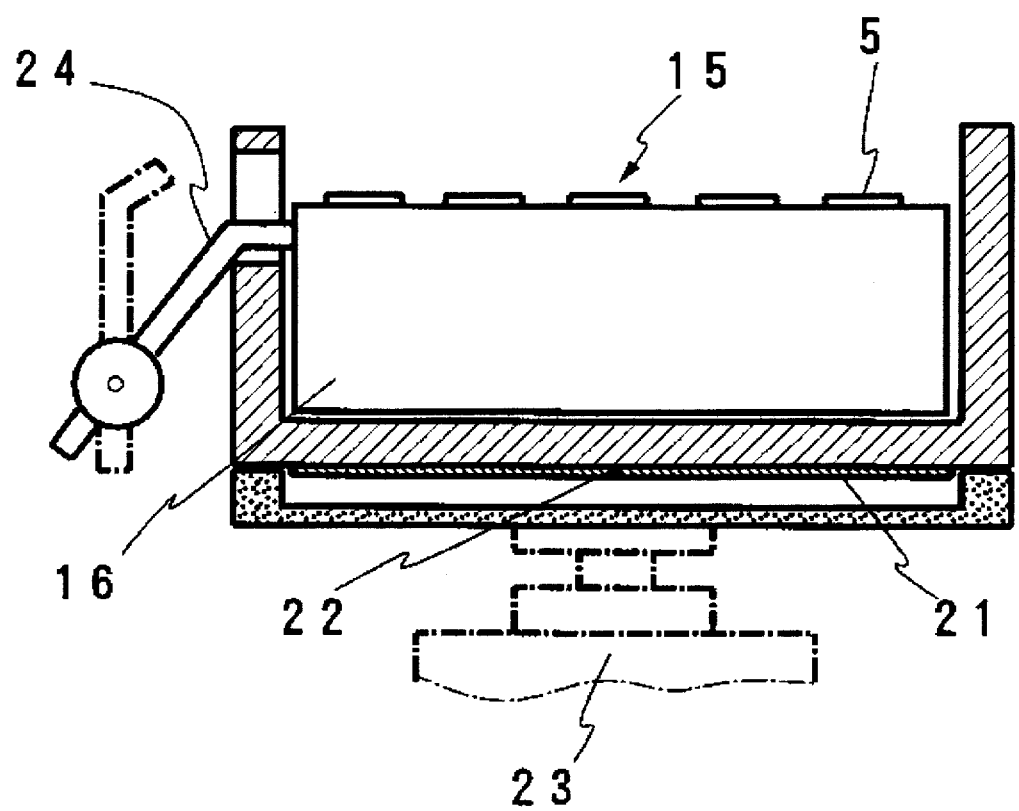
FIG. 5 is a schematic section of one embodiment of the structure of an incubator part.

FIG. 5 is a schematic section showing an incubator part 15 which comprises a heater 21 to heat the reaction vessel 5, a sensor 22 to control temperatures, a shaking device 23 for shaking the whole incubator part and a fixing element 24 to fix a measurement rack 16 while shaking.

In the incubator part 15, the reaction vessel 5 housed in the measurement rack 16 is heated at a suitable temperature for a certain period of time. Although the above-mentioned shaking device may not always be necessary, installation thereof is preferable in view of uniform hybridization in the reaction vessel and shortened reaction time.

The B/F separation unit E comprises the aforementioned sample-reagent unit A, the sample-reagent dispense unit B and the hybridization unit D.

Alternatively, it comprises a discharge nozzle and a washing solution nozzle to be installed in the arm part which is movable in the directions of the X-Y-Z axes, a device to suck the content of the reaction vessel after hybridization with said discharge nozzle for discharging same to the outside and to suck a washing solution from a washing solution reservoir with a washing solution nozzle to inject same into said reaction vessel, and the circulation mechanism of the aforementioned hybridization unit.

The light measurement unit F comprises a mechanism for sucking an enzyme substrate from a reagent pack in the reagent cassette with a tip nozzle equipped with a tip of a sample-reagent dispense unit and injecting same into the reaction vessel after B/F separation, a circulation mechanism for said hybridization unit, and a light measurement device to measure an optically measurable change in the reaction vessel.

Figure 6:
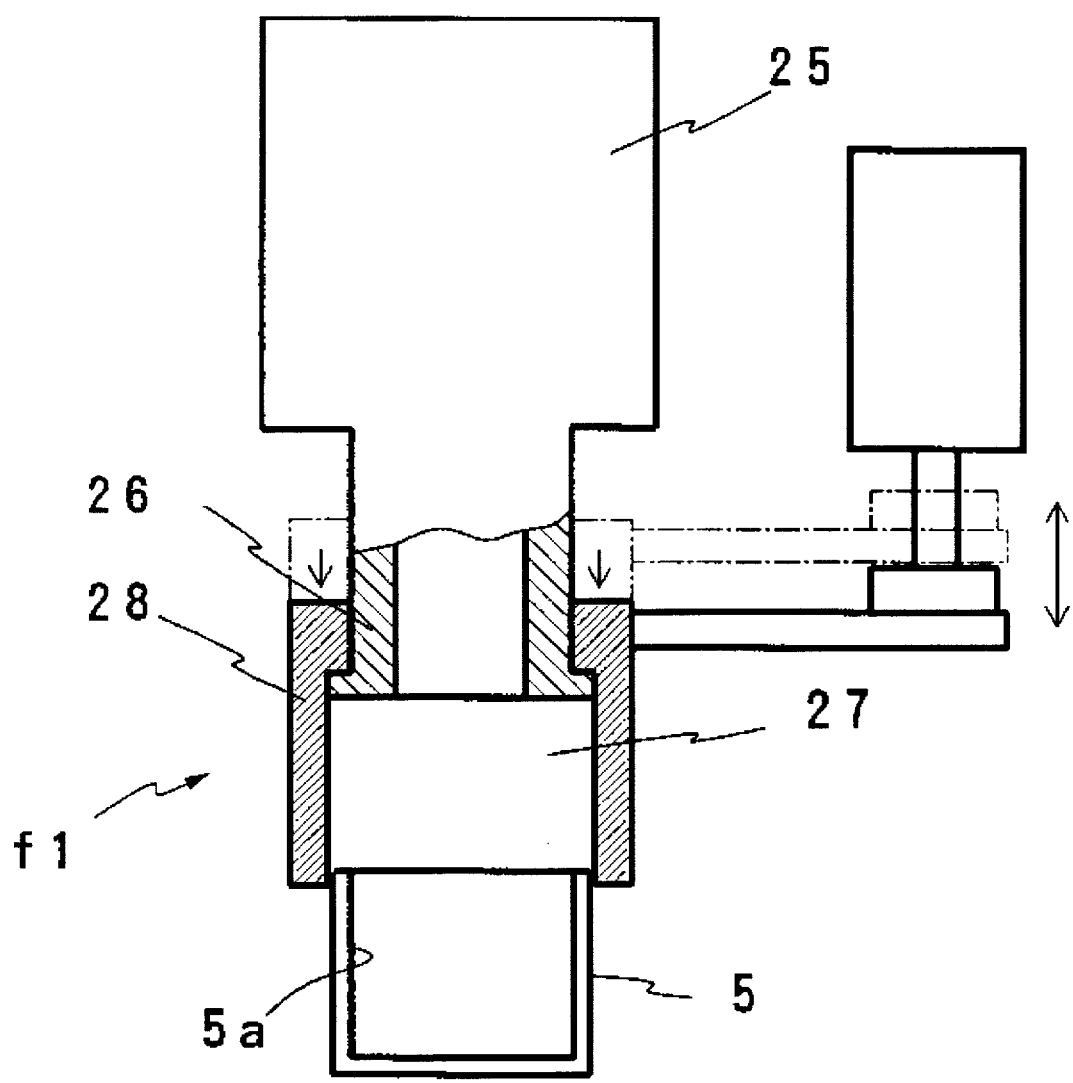
FIG. 6 is a schematic section of one embodiment of the structure of a light measurement unit.

FIG. 4 shows an embodiment wherein a light measurement device is placed on a transport line 20 of a hybridization unit circulation device. In the present invention, a light measurement device usable in a regular DNA probe hybridization method can be suitably used. When detection of an emitted light is aimed, a light measurement device f1, as shown in the schematic section of FIG. 6, wherein a gap 27 between a light receiving part 26 in a light detection part 25 and an opening 5a in a reaction vessel 5 is easily covered by a light-shielding member 28, is preferably used, since outside light and stray light from other reaction vessels in the measurement rack can be shielded to enable high precision measurement of a slight light change.

The apparatus for an automated assay of a DNA probe having the above-mentioned structure can be suitably applied to a color measurement method wherein an absorbance of an emission caused by reaction of NBT (nitro blue tetrazolium), BCIP (5-bromo-4-chloro-4-indolylphosphate) or the like (which is a color developing reagent) with a probe marked with an enzyme is measured at about 570 nm, a fluorescence measurement method wherein a chelating agent such as lanthanoid or europium (which is a fluorescent pigment) is marked and fluorescence excited by an ultraviolet ray irradiation is measured, an emitted light measurement method wherein an emission caused by reacting luminol, a dioxetane derivative or the like (which is a light emitting substrate) with a probe marked with an enzyme is measured and other methods.

As the detector to be used for light measurement, a light source, an interference filter, a light receiving element or the like may be selected according to the measurement method to be employed.

In addition, the present inventors took note of the gap formed between the light receiving part in the light detection part and a sample container in conventional light measurement apparatuses and the following investigation resulted in the completion of a light measurement device suitable for the measurement apparatus of the present invention.

The light measurement device suitable for the measurement apparatus of the present invention comprises a device for detecting a light emission which involves a light receiving part at the head portion thereof, a hollow light-shielding which is movable along the peripheral surface of the light receiving part, and a measurement sample container (reaction vessel) disposed with its opening in an opposite relation to the head portion of the light receiving part, wherein the gap formed between the head portion of the light receiving part and the upper end of the sample container can be easily covered by moving the hollow light-shielding member during light measurement.

In the light measurement device, a marker is, for example, a substance which emits light by itself, a substance which emits light by the action of other substance or a substance which emits light upon reaction to convert a light emitting substrate to a light emitting substance. In the light measurement, a measurement sample such as a biological component is bound with a substance which is labeled with a marker and which specifically binds to said biological component by specific binding reaction etc., and the light emission by the marker substance or that of a light emitting substance produced by the action of the marker substance is measured.

The relation between the above-mentioned measurement sample such as a biological component and a substance which specifically binds therewith is generally called ligand-receptor system. In the present invention, it refers to nucleic acid-nucleic acid group such as DNA (or RNA) and complementary DNA (or complementary RNA).

The method for emitting light includes, for example, a method utilizing light emission by an organism or chemical light emission.

The light emission by an organism means irradiation of visible light by a living organism and examples of the light-emitting organism include light emitting bacteria, fungi, protozoans such as Noctilcaceae and insects such as firefly.

The chemical light emission means a phenomenon in which a light is emitted by atoms or molecules excited by an energy caused by chemical reactions and examples of the chemical light emitting substance (substrate) include luminol, esters of acridinium compound, stabilized dioxetane, peroxalic esters and so on.

Figure 7:
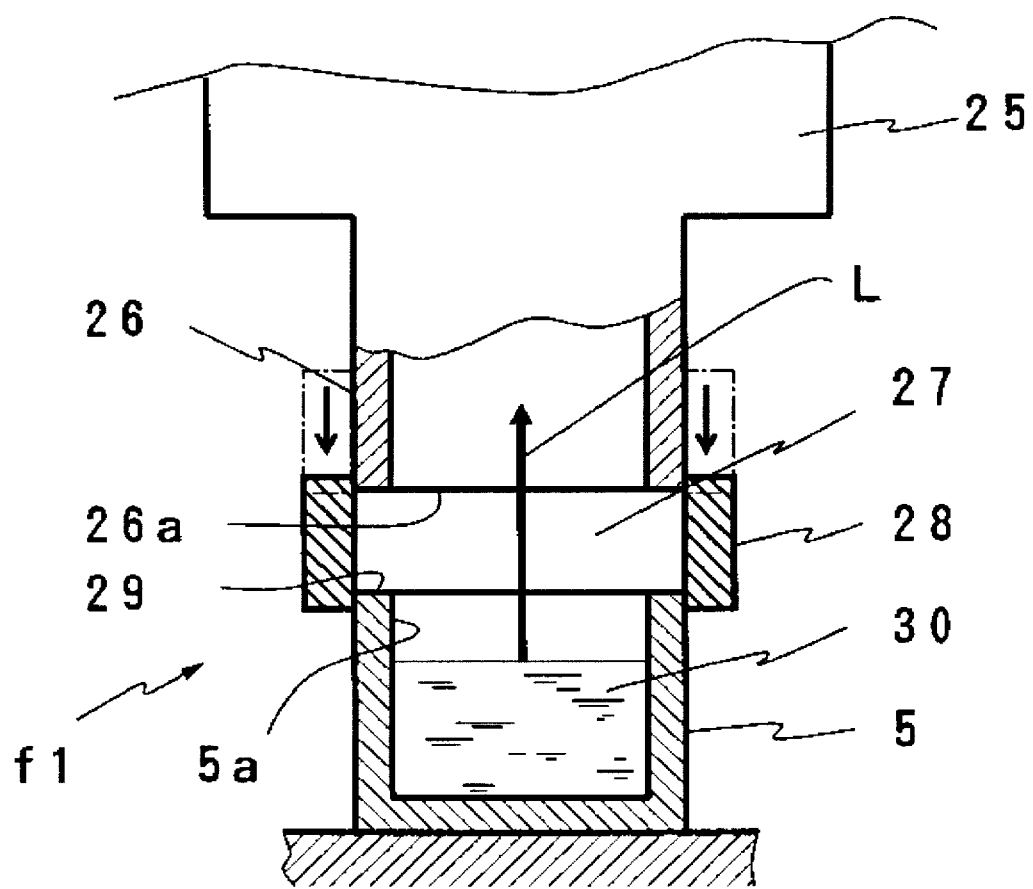
FIG. 7 is a schematic partial section showing the basic structure of the light measurement device suitable for the present invention.

The light measurement device comprises, as shown in the schematic partial section of FIG. 7, a means for emitted light detection part 25 having a light receiving part 26 at the head portion thereof, a hollow light-shielding member 28 which is movably provided along the peripheral surface of the light receiving part 26, and a reaction vessel 5 containing a measurement sample 30 and disposed with its opening 5a in an opposite relation to the head portion 26a of the light receiving part.

In this light measurement device, a gap 27 is formed between the head portion 26a of the light receiving part and the upper end 29 of the reaction vessel.

According to the light measurement device of the structure as described, the hollow light-shielding member 28 is moved in the direction of an arrow (downward) during the light measurement so that at least the gap 27 is covered thereby, thus preventing invasion of an outside light into the gap 27, with the result that an emitted light L from the biological component in the measurement sample 30 can be measured with high precision.

The emitted light detection part 25 to be used for the light measurement device may be any insofar as it permits detection of a weak light with high sensitivity and an emitted light detection element such as a photomultiplier can be suitably used. The emitted light detection part 25 desirably has the light receiving part 26 extruding in a tubular shape from the head portion thereof.

The light-shielding member 28 is formed in a hollow shape from a light-shielding material so as to make it movable along the tubular light receiving part 26 and installed in a movable fashion to the longitudinal direction of the peripheral surface of the light receiving part 26, preferably fitted in a slidable relation. The inside of the light-shielding member 28 is preferably black to absorb light.

The light-shielding member 28 is moved by a manual handling of an operator or by a mechanical means using an outside drive.

It is preferable that no vibration has effects on the emitted light detection part 25 during the movement.

The reaction vessel 5 is subject to no particular limitation insofar as it has a hole-like opening 5a enabling accommodation of measurement samples and that having at least one opening 5a such as a microplate may be suitably used. The measurement rack may contain one or more vessels 5. The vessel 5 and the measurement rack may be transparent or colored. When a plurality of openings are positioned closely together when in use, colored ones, particularly black ones, are preferable in terms of inhibition of a stray light from other samples.

A measurement target sample and a measurement reagent from a biological component are kept in the reaction vessel 5. The biological component in the sample emits light upon reaction with the reagent, which light is emitted to the outside of the vessel 5 through the opening 5a.

The emitted light is detected by the emitted light detection part 25 through the light receiving part 26. The structure of the invention wherein a gap 27 between the light receiving part 26 and the upper end 29 of the vessel is covered with a hollow light-shielding member 28 has an effect that an outside light and a stray light can be shielded to result in a high precision measurement of the emitted light.

For higher levels of outside light shielding effect, the light measurement device preferably has the following structure.

That is, the light-shielding member is fit on the outer surface of the tubular light receiving part in a sliding relation. Yet, even such a slidable fitting may leave a very small clearance. When a very high precision light measurement is aimed, the light coming through this tiny gap also should be shielded.

Figure 8A:
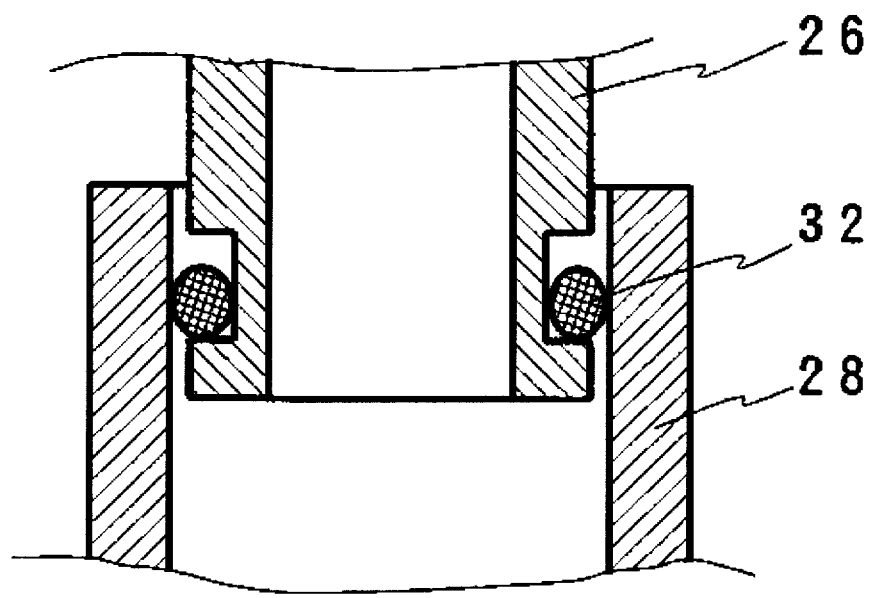
FIG. 8 is a schematic section of a structure for shielding a light from the gap between a light receiving part and a light-shielding member.
Figure 8B:
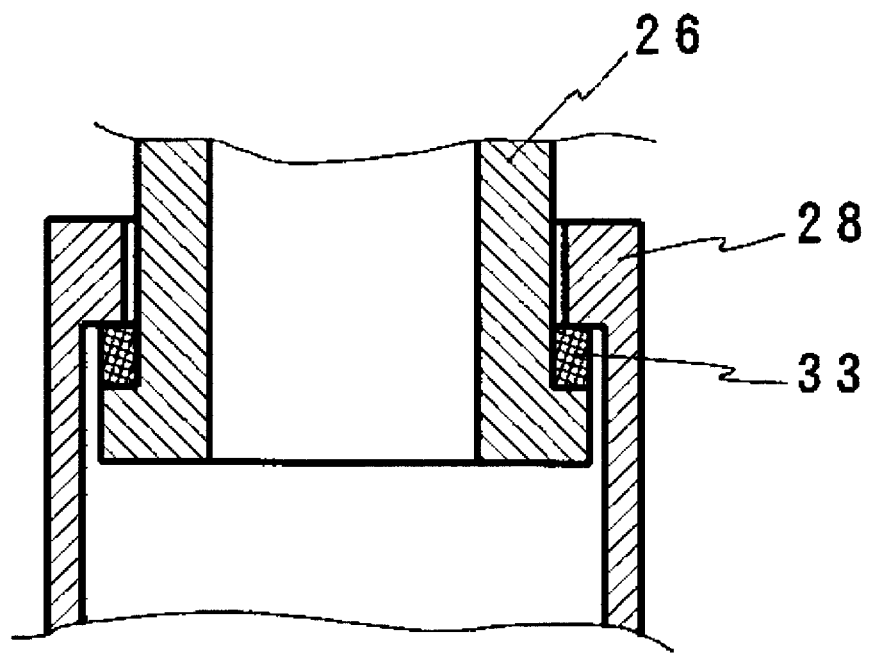

FIG. 8 shows one embodiment having a shielding structure to this effect, in which FIG. 8A shows a shielding structure with an 0-ring 32 (prepared from a light-shielding material) applied on the side surface of the light receiving part 26 and FIG. 8B shows a shielding structure with a resilient light-shielding circular synthetic resin member 33 applied along the periphery of the bottom end portion of the light receiving part 26.

In addition, shielding of the light through a very small gap between the vessel and the light-shielding member should be considered.

Figure 9A:
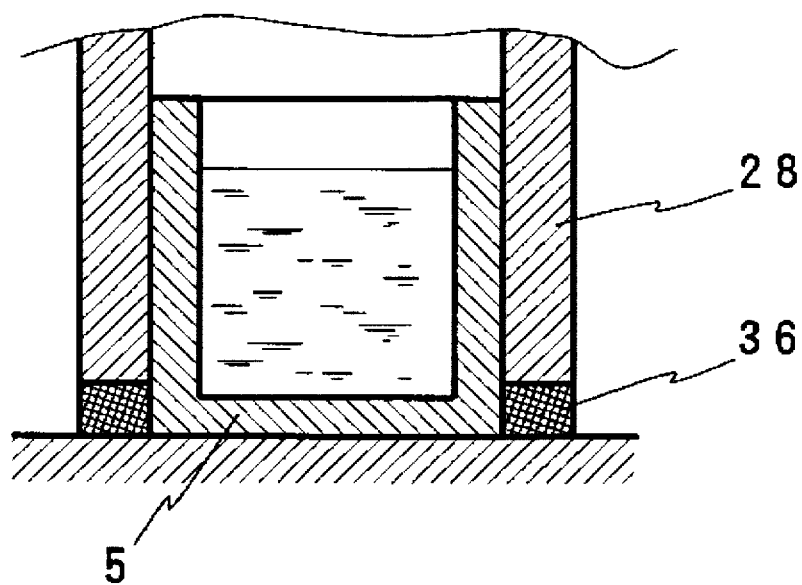
FIG. 9 is a schematic section of a structure for shielding a light from the gap between a reaction vessel and a light-shielding member.
Figure 9B:
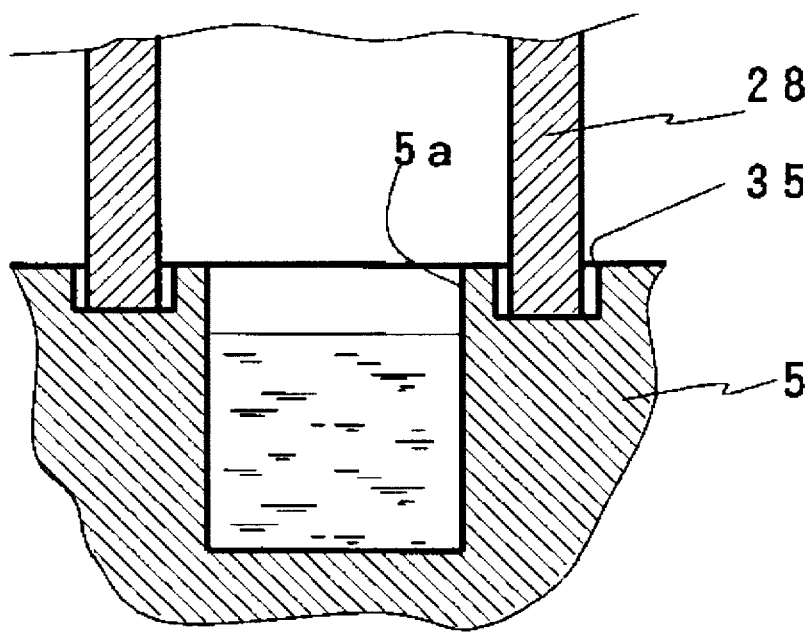

FIG. 9 shows one embodiment having a shielding structure to this effect, in which FIG. 9A shows a shielding structure with a resilient light-shielding circular synthetic resin member 36 applied to the bottom end portion of the light-shielding member 28 and FIG. 9B shows a shielding structure where a circular groove 35 is formed along the periphery of the opening 5a of the reaction vessel 5 and a light-shielding member 28 is loosely fitted in the circular groove 35. In particular, the latter light-shielding structure permits more accurate positioning of the light detection means and a reaction vessel and will desirably contribute to more improved measurement precision.

The aforesaid circular groove may be formed along the periphery of the vessel holder on the measurement rack holding the reaction vessels.

Further, a construction wherein the reaction vessel or the measurement rack holding the vessel is placed on a table on which a conveyor runs permits continuous light measurement of the samples and improved work efficiency.

The construction of the light measurement device of the present invention as described permits a high level of light-shielding effect with a simple light-shielding structure and reduction of the cost necessary for shielding the light. In addition, the light-shielding member is movably adapted, with the effect that the reaction vessel can be replaced with ease unless the light measurement is underway. Since the position of the vessel can be fixed, it can be easily and accurately set at the position corresponding to the light receiving part.

Hence, an automated sequential transfer of the vessels to and from the predetermined position enables continuous high precision light measurement of a plurality of samples.

An example of the light measurement using the aforesaid measurement device is given as follows.

Stabilized dioxetane which emits light by alkaline phosphatase as a catalyst was used as a measurement sample and its chemical light emission was measured by a photon counting method using a photomultiplier as an emitted light detection part.

Figure 10:
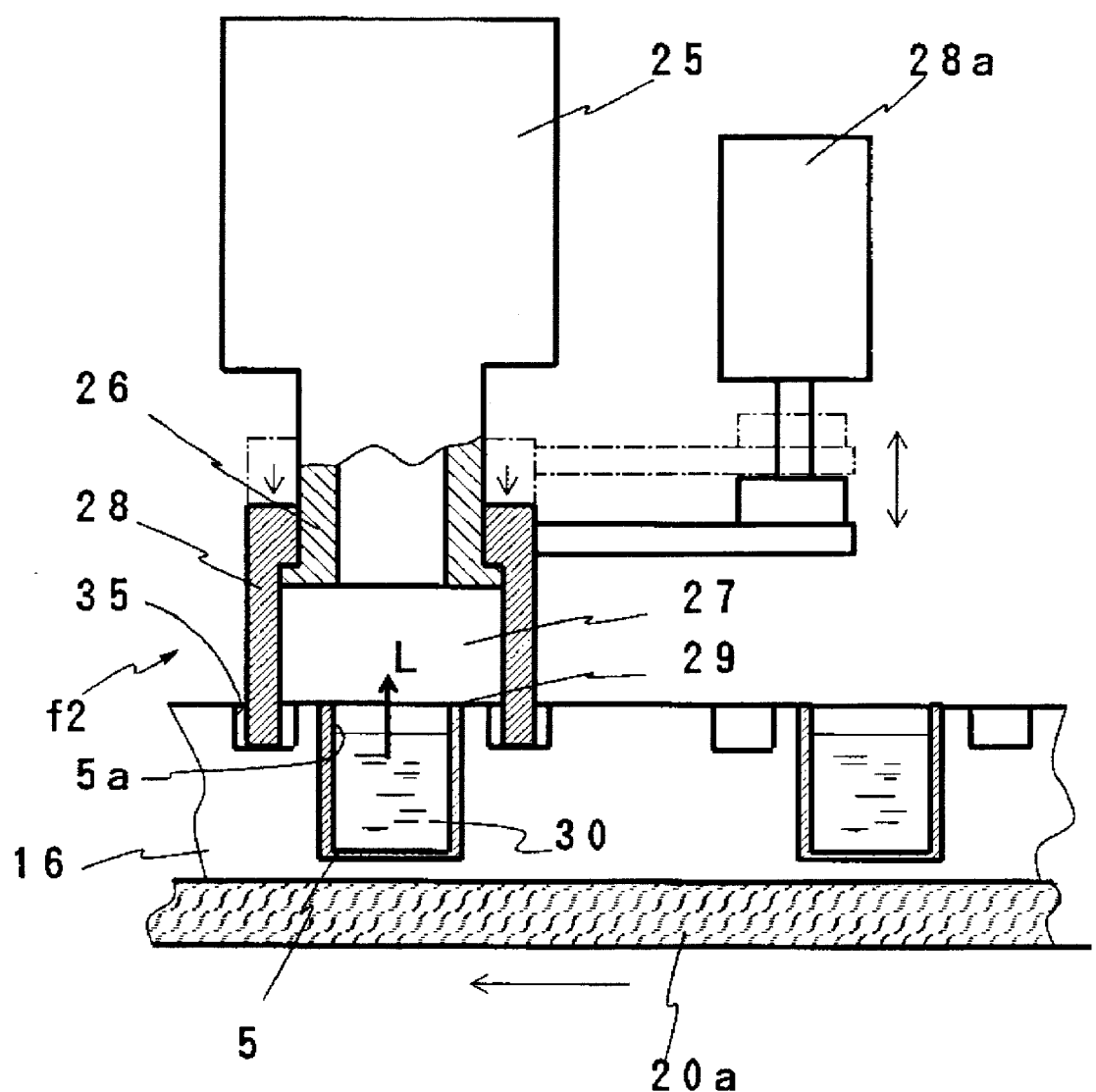
FIG. 10 is a schematic partial section showing one embodiment of a light measurement device in use which is suitable for the present invention.

FIG. 10 schematically shows the measurement device in use, wherein f2 is a light measurement device comprising an emitted light detection part (photomultiplier) 25 having a 14 mm outer diameter cylindrical a light receiving part 26 positioned at the head portion thereof, a tubular light-shielding member 28, which is movably fitted on the peripheral surface of the light receiving part 26 and slides in the direction of the axis by an outside driving device 28a, a reaction vessel 5 (microplate) containing said measurement sample 30 and having a 7 mm aperture diameter opening 5a disposed in an opposite relation to the head portion 26a of the light receiving part 26, and a measurement rack 16 holding a plurality of reaction vessels 5. A circular groove 35 concentric with the opening 5a of the reaction vessel 5 held by the measurement rack 16 is formed on the top surface of the rack. The measurement rack 16 is positioned on a belt conveyor 20a which moves in a longitudinal direction.

Figure 11:
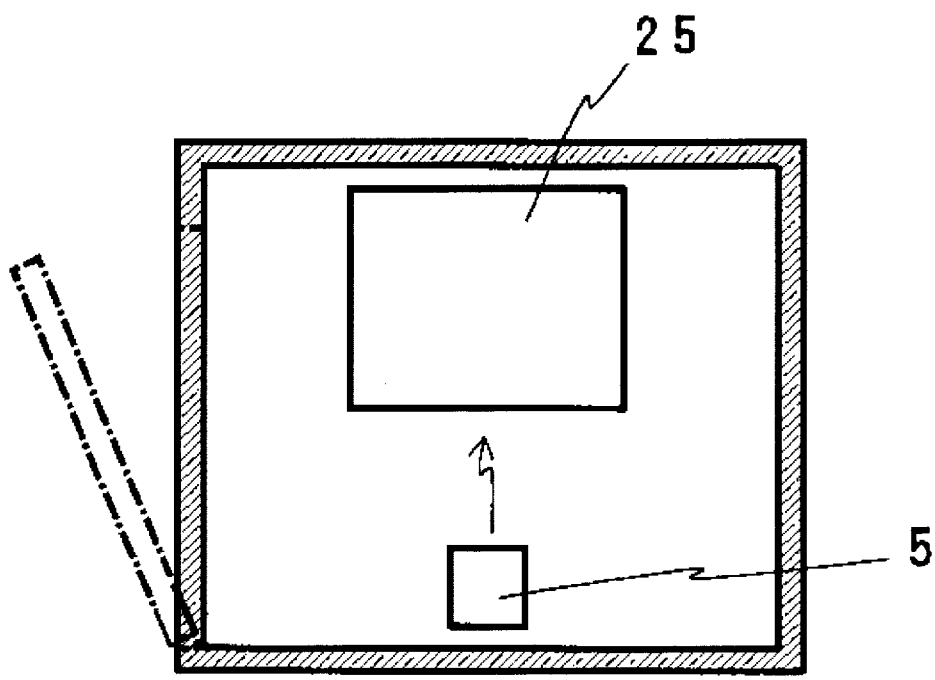
FIG. 11 is a schematic section of a structure for shielding a light, as employed in a conventional light measurement device.
Figure 12:
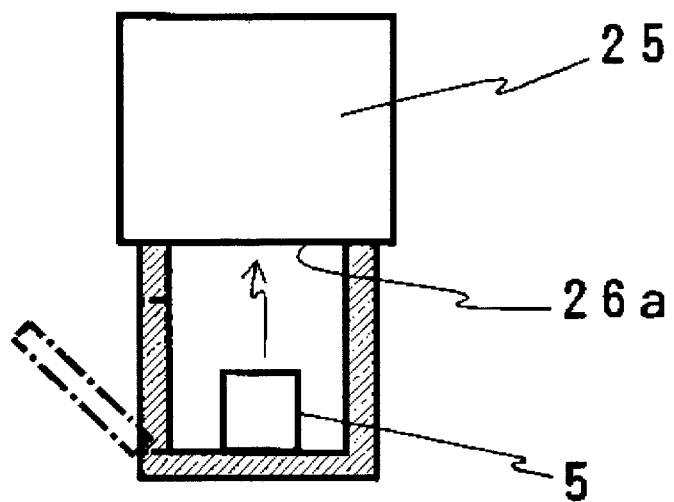
FIG. 12 is a schematic section of another structure for shielding a light, as employed in a conventional light measurement device.

The measurement of the chemical light emission was performed as follows. The opening 5a of the reaction vessel 5 was set in such a manner that it coaxially coincides with the light receiving part 26 of the light detection photomultiplier 25. Then, the light-shielding member 28 was moved in the direction of an arrow by the outside driving device 28a, thereby covering the gap 27 formed between the head portion 26a of the light receiving part 26 and the upper end 29 of the reaction vessel, and loosely fitted in the bottom end portion of the light-shielding member 28 in adhesion to the bottom surface of the circular groove 35. While maintaining this state, the photomultiplier 25 was activated, whereby the chemical light emission L from the stabilized dioxetane in the measurement sample 30 contained in the opening 5a in the reaction vessel 5 was introduced into the light receiving part 26 and measured by a photon counting method. After the measurement, the light-shielding member 28 was moved back to its original position in the light receiving part 26 by the outside driving device 28a and the belt conveyor 20a that carries the measurement rack 16 was moved in the direction of an arrow to set a next determination sample in the opening 5a in the reaction vessel 5 in coaxial concord with the light receiving part 26. The above steps were repeated to perform light measurement on the chemical emission from the measurement samples contained in plural microplates held by the measurement rack. As a reference, the same measurement as above was performed using an apparatus which:(a) did not shield the gap (Comparative Example 1), (b) partly shielded the gap as shown in FIG. 12 (Comparative Example 2), and (c) covered the entire light measurement device as shown in FIG. 11 with a light-shielding material (Comparative Example 3). The results are shown in Table 1.

TABLE 1

|  | Ex. | Comparative Exs. | | |
| --- | --- | --- | --- | --- |
|  | 1 | 1 | 2 | 3 |
| Signal (count/sec) | 45700 | 43800 | 35300 | 100.3 |
| Noise (count/sec) | 29 | 270 | 35 | 0.33 |
| Signal/Noise | 1570 | 162 | 1010 | 304 |
| Measurement time (sec/sample) | 2 | 2 | — | 8 |

As evidenced in Table 1, the method of Example 1 prevents invasion of an outside light from the gap as well as shields a stray light from a sample other than the measurement target, exhibiting a precision measurement as high as or higher than that of the apparatus of Comparative Example 2.

In addition, a highly efficient workability as compared with the light measurement apparatus of Comparative Example 3 was obtained.

The construction of the present invention as described permits a high level of light-shielding effect with a simple light-shielding structure and reduction of the cost necessary for the equipment for shielding light. In addition, the light-shielding member is movably adapted, with the effect that reaction vessels can be replaced with ease, the location of the vessels can be fixed, and they can be easily and accurately set at the position corresponding to the light receiving part.

Hence, an automated sequential transfer of the vessels to and from the predetermined position enables continuous high precision measurement of a plurality of samples, improved work efficiency and work cost reduction.

Further, another light measurement device suitable for the apparatus of the present invention is exemplified by the following.

That is, a light measurement device comprising; an emitted light detection part, a tubular light receiving part to introduce the light emitted by a sample into said emitted light detection part, a hollow light-shielding member movable along the peripheral surface of said tubular light receiving part, a movable shutter that opens a light path through said tubular light receiving part only when the emitted light is measured, and a vessel containing a measurement sample and disposed with its opening in opposite relation to the tubular light receiving part, the emitted light detection part preferably comprising a means for photoelectric transfer of the emitted light and a means for determining the emitted light from the photoelectric transfer value.

A light measurement using said light measurement device is explained by referring to the following embodiment.

Figure 13:
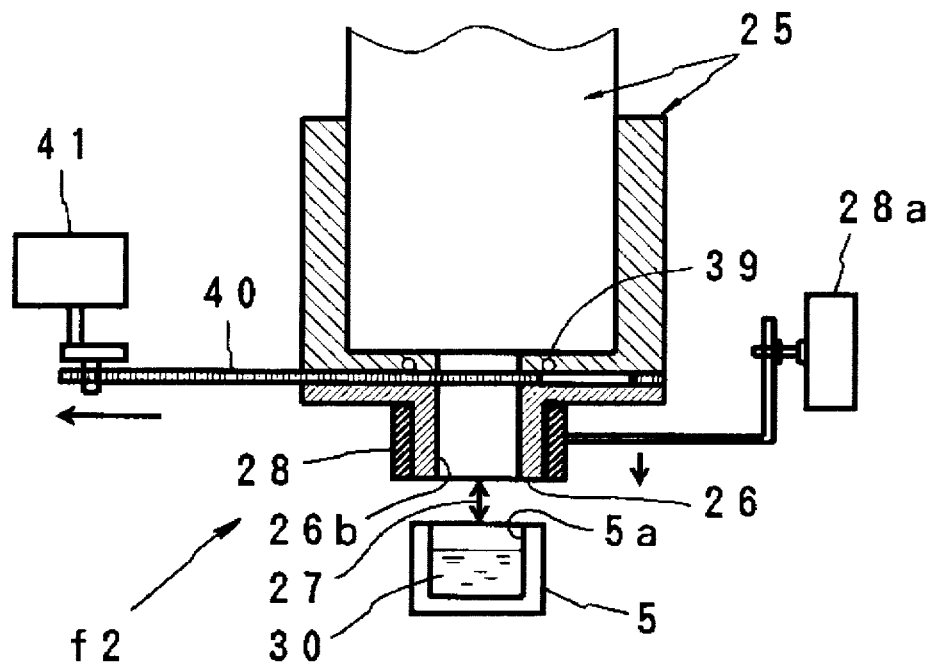
FIG. 13 is a schematic partial section showing the basic structure of another embodiment of a light measurement device in use which is suitable for the present invention.

FIG. 13 is a cross section of one embodiment of the emitted light measurement device of the present invention, wherein f2 is an emitted light measurement device comprising an emitted light detection means 25, a light receiving part to introduce the light emitted by a sample into said emitted light detection means, a hollow light-shielding member movable along the peripheral surface of said light receiving part 26, a movable shutter 40 that opens a light path 26a through said light receiving part only when an emitted light is measured and a reaction vessel 5 containing a measurement sample 30 and disposed within its opening 5a in opposite relation to the light passage.

The shutter 40 is coupled to a shutter driving device 41 and the hollow light-shielding member 28 is coupled to a light-shielding member driving device 28a.

The emitted light detection part 25 is not subject to any particular limitation insofar as it can detect a light emission from a sample and can measure its amount, and conventionally known detection devices can be used. In the present invention, a device capable of detecting a weak light with high sensitivity, which, for example, comprises a device for photoelectric transfer, such as photomultiplier, and a device for determining the light amount from the transfer value, such as a photon counter, is suitably used.

The light receiving part 26 is a hollow member having a tubular shape; a light entry on one end of the emitted light detection part 25 is outwardly protruded either integrally from the hollow member or another member is joined thereto to protrude to the outside direction, the hollow part being the light path 26b to introduce a light emission from a sample to the emitted light detection part 25.

The cross section of the light receiving part is not subject to any limitation and it may be a circle or a polygon such as triangle, rectangle or the like. In the present invention, it is preferable that the light receiving part have a similar figure to the shape of the opening of a reaction vessel that is usually a cylindrical shape.

The hollow member may be made of any material so long as it does not absorb the light emitted by a sample and aluminum, stainless or the like is preferably used.

The shutter 40 is passed through a gap between the emitted light detection part 25 and the light receiving part 26 and can open or close the light path 26b through the light receiving part 26. In the present invention, the structure thereof may be any so long as it can open or close the light path 26b. For example, the structure thereof may be that of a shutter or a diaphragm of a camera. The gap through which a shutter is inserted may be formed in the light receiving part.

Such shutter 40 may be a plate having almost the same size as said gap and a width and a thickness permitting insertion thereof through the gap. The shutter is preferably provided with a through-hole having almost the same size as and a shape similar to the cross section of the light receiving part and moved perpendicular to the light path 26b until the through-hole coincides with the light path 26b to open the light path.

The material of the shutter is not particularly limited so long as it can shield off the light and stainless, aluminum, iron etc. are suitably used.

The surface of the shutter 40 is preferably black to absorb light.

A shutter driving device 41 is coupled to the shutter 40. Upon activation of the shutter driving device 41, the shutter 40 is moved in the direction (of an arrow) to open or close the light path 26b.

It is desirable that the shutter driving device 41 should comprise a device for controlling at a step number which does not give vibration to the light detection part 25, such as a stepping motor.

In the structure as described, seal may be formed by an 0-ring 39 or the entirety of the shutter and the driving device may be light-shielded, so as to prevent an outside light from entering into the light detection part 25 through the gap formed for inserting the shutter 40. By employing this structure, shielding of an outside light can be effectively attained.

The light-shielding member 28 is a light-shielding hollow member which is fitted on the peripheral surface of the light receiving part 26 in a movable manner in a longitudinal direction, preferably in a slidable manner.

The light-shielding member may be made of any material insofar as it can shield off light and stainless, aluminum etc. are suitably used.

The inside of the light-shielding member 28 is preferably black to absorb light.

A light-shielding member driving device 28a is coupled to the hollow light-shielding member 28. Upon activation of the light-shielding member driving device 28a, the light-shielding member 28 is moved in the direction of the axis (direction of an arrow) along the peripheral surface of the light receiving part.

The reaction vessel 5 is not subject to any particular limitation insofar as it has an opening 5a enabling accommodation of a measurement sample and having at least one opening 5a. For example, a microplate having plural openings is conveniently used with less labor for exchanging vessels. The measurement rack may be used with at least one reaction vessel held therein. The vessel and the measurement rack may be transparent or colored. When a plurality of openings are positioned closely together colored ones, particularly black ones, are preferable in terms of inhibition of stray lights from other samples.

A measurement target sample, a measurement reagent from biological component etc. are kept in the reaction vessel 5. The biological component in the sample emits light upon reaction with the reagent etc., which light being emitted to the outside of the vessel 5 through the opening 5a.

In the emitted light measurement device suitable for the present invention, the shutter 40 closes the light path 26b through the light receiving part 26 of the light detection part 25 when measurement is not underway, as shown in FIG. 13. Invasion of an outside light from the gap 27 into the light receiving part 26 of the emitted light measurement part 25 can be prevented even when light shielding of the entire light measurement device is insufficient, with the result of void degradation or deterioration of light receiving elements.

When the emitted light measurement is performed, a reaction vessel 5 containing a measurement sample 30 is placed at a predetermined position with its opening 5a in opposite relation to the light receiving part 26 of the emitted light measurement part 25, thus forming a gap 27 between the light receiving part 26 and the vessel 5. Upon activation of the light-shielding member driving device 28a, the hollow light-shielding member 28 carried on the peripheral surface of the light receiving part 26 slides in the downward direction of the axis of the light receiving part (direction of an arrow) to cover at least the gap 27 between the light receiving part 26 and the vessel 5, whereby the gap 27 is light-shielded and invasion of an outside light into the light receiving part 26 of the emitted light measurement part 25 can be prevented.

Figure 14:
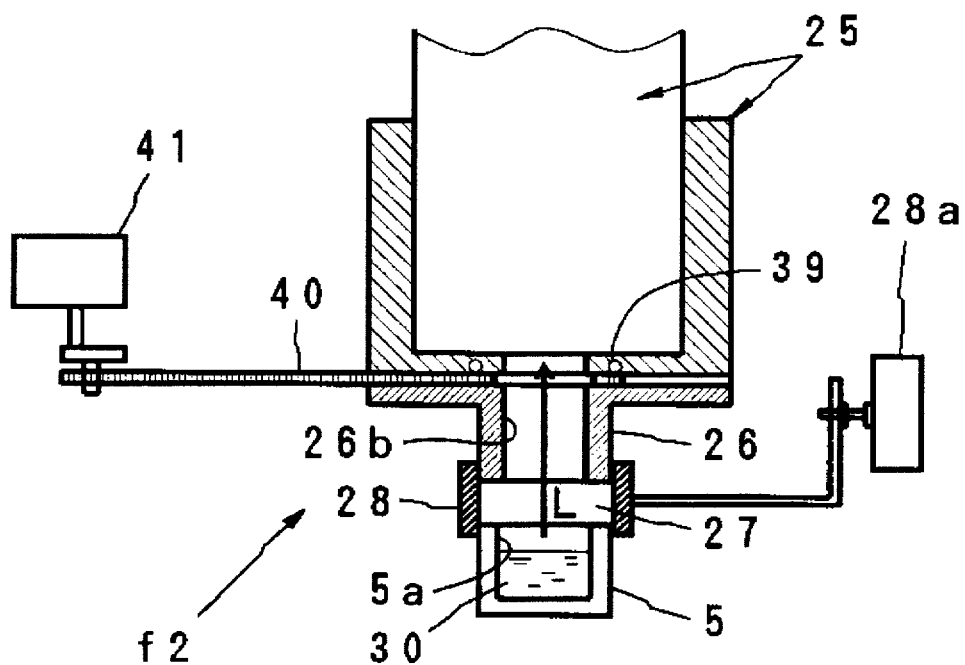
FIG. 14 is a schematic partial section for explaining the action mechanism of a shutter and a light-shielding member in a light measurement device.

Upon activation of the shutter driving device 41, the shutter 40 is moved the direction of an arrow to open the light path 26b through the light receiving part 26, with the result that the light L emitted from the measurement sample 30 is introduced into the emitted light measurement part 25, as shown in FIG. 14.

The emitted light to be introduced into the emitted light measurement part 25 is detected by a light receiving element and measured for its amount by a photomultiplier (not shown) and a photon counter (not shown) to determine the light amount based on the transfer value given by the photomultiplier.

Even when a microplate having a plurality of openings is used for the emitted light measurement as described, shielding of the gap 27 prevents invasion of an emitted light (stray light) from samples other than the measurement target sample into the light receiving part, thus resulting in no occurrence of noise.

As described above, invasion of an outside light into the light receiving part of the emitted light detection device can be prevented both when an emitted light is being measured and when not. In addition, invasion of a stray light into the light receiving part of the emitted light detection device can be prevented when the measurement is underway. Accordingly, invasion of an outside light or a stray light into the light receiving part of the emitted light detection device can be prevented even when the light shielding of the whole apparatus is insufficient, and degradation of light receiving elements and generation of noise can be eliminated. What is more, since a light-shielding case is not necessary, the reaction vessel can be accurately positioned and the emitted light measurement precision can be greatly enhanced.

In addition, a simple light-shielding structure without a light-shielding case makes the device compact and reduces the production cost.

If the shutter driving device 41 is activated prior to the emitted light measurement, the light path through the light receiving part of the emitted light measurement part 25 is opened before closing of the gap 27 between the light receiving part and the vessel 5, letting outside light and stray light invade into the light path to degrade measurement precision. Accordingly, it is preferable that the shutter driving device 41 be activated simultaneously with or after the activation of said light-shielding member driving device 28a.

For higher levels of outside light shielding, the emitted light measurement device suitable for the apparatus of the present invention preferably has the structure for light shielding as described in detail for the light measurement device f1 or that using an O-ring or a circular groove (FIGS. 8 and 9).

Further, a construction wherein the reaction vessel or the measurement rack holding the vessel is placed on a table on which a conveyor runs, permits continuous light measurement of the samples and improved work efficiency.

A light measurement according to the light measurement device f2 was performed as follows:

EXPERIMENT 1

Using the emitted light measurement device of FIG. 14, the degree of outside light invasion when light measurement was not underway was determined by a photon counting method. The light measurement device f2 then had the light path 26b closed by the shutter 40 and the light-shielding member 28 positioned above the light receiving part.

For comparison, the light-shielding effect by the shutter was determined when a 40 W indoor fluorescent light was lighted at a distance of 4 m, when a 10 W indoor fluorescent light was lighted at a distance of 2 m and when the both were not lighted. The results are shown in Table 2.

TABLE 2

|  | Shutter opened | Shutter closed |
|---|---|---|
| 40 W indoor fluorescent light on | 20000000 cps or above | 0 cps |
| 10 W indoor fluorescent light on | 10000000 cps or above | 0 cps |
| 40 W and 10 W indoor fluorescent lights off | 500000 cps | 0 cps |

(measured for 1 second, cps = count per second)

As is evident from Table 2, the shutter shielded the outside light almost completely and additional shielding such as a cover on the entire device was not necessary except to keep the shutter in a closed position unless light measurement was being done.

EXPERIMENT 2

Using stabilized dioxetane which emits light by alkaline phosphatase as a catalyst, as a measurement sample, its chemical light emission was measured by a photon counting method using a photomultiplier as a light receiving element.

Figure 15:
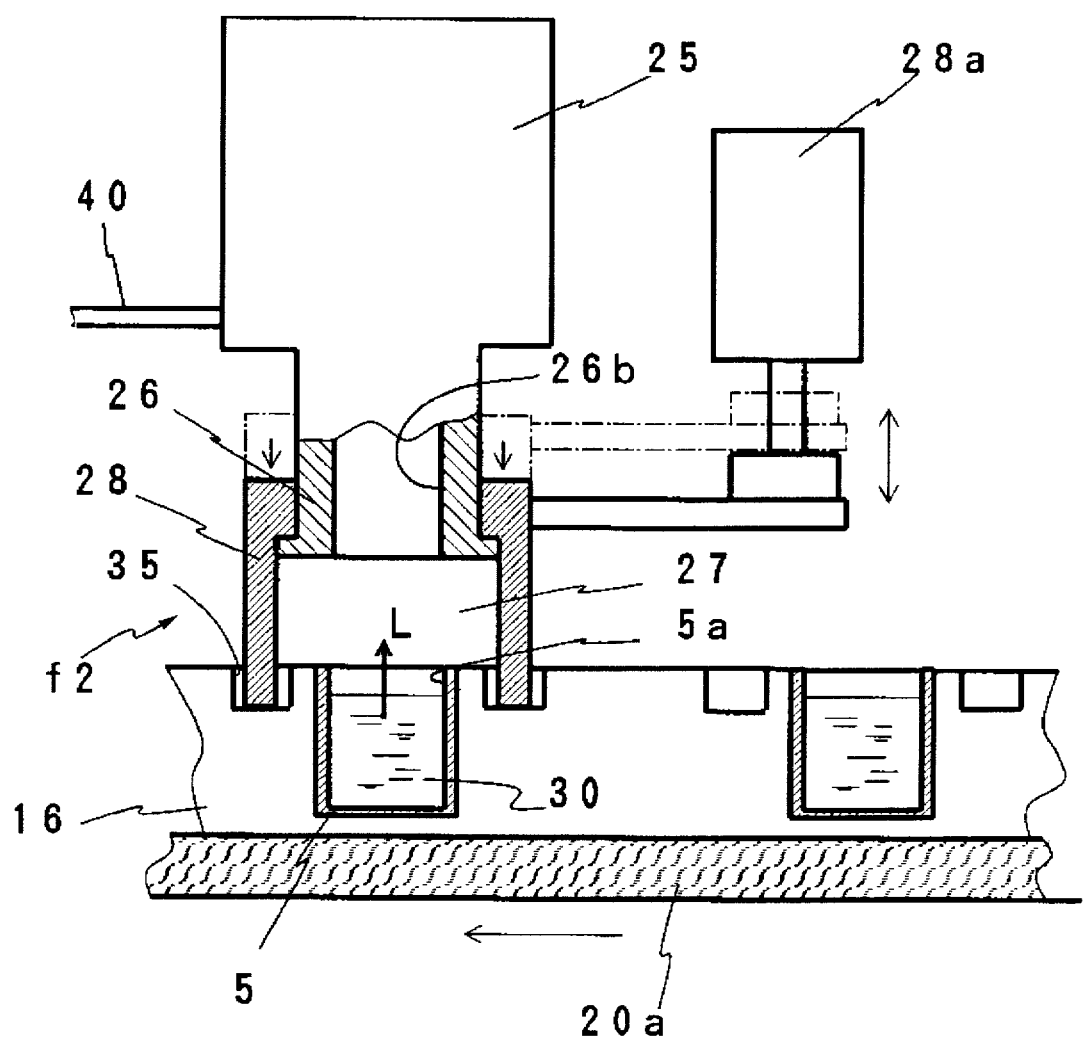
FIG. 15 is a schematic partial section showing another embodiment of a light measurement device in use which is suitable for the present invention.

In this experiment, an emitted light measurement device as shown in FIG. 15 was used. While FIG. 15 does not show details of the shutter structure, it is the same as that shown in FIG. 13. The emitted light measurement device f2 comprised an emitted light detection part 25 having a 14 mm outer diameter and 7 mm inner diameter cylindrical light receiving part 26 at the head portion thereof, a tubular light-shielding member 28, which was movably fitted on the peripheral surface of the light receiving part 26 and slid in the direction of the axis (direction of an arrow) by a light-shielding member driving device 28a, a 1-well microplate 5 containing a measurement sample 30 and having a 7 mm aperture diameter opening 5a disposed in opposite relation to the light receiving part 26, and a measurement rack 16 holding said microplate. A circular groove 35 concentric with the opening 5a of the microplate 5 held by the measurement rack 16 was formed on the top surface of the rack. The measurement rack 16 was placed on a belt conveyor 20a and moved in a longitudinal direction.

The measurement of the chemical light emission was performed as follows. The opening 5a of the microplate 5 was set in such a manner that it coaxially coincided with the light receiving part 26 of the light detection part 25. Then, the light-shielding member 28 layered on the periphery of the light receiving part 26 was moved in the direction of an arrow by the light-shielding member driving device 28a, thereby covering the gap 27 formed between the head portion 26a of the light receiving part 26 and the opening 5a of the microplate and loosely fitted in the bottom end portion of the light-shielding member 28 in adhesion to the bottom surface of the circular groove 35. Then, the shutter 40 was moved by the shutter driving device 41 to let it open. A photomultiplier in the emitted light measurement part was activated, whereby the chemical light emission L from the stabilized dioxetane in the measurement sample 30 contained in the microplate 5 was introduced into the light receiving part 26 and measured by a photon counting method.

After the measurement, the shutter 40 was moved back to its original position by the shutter driving device 41 to close the light path through the light receiving part 26 and the light-shielding member 28 was moved back to its original position by the light-shielding member driving device 28a. The belt conveyor 20a carrying the measurement rack 16 was moved in the direction of an arrow to set a next measurement sample contained in a microplate with its opening 5a in a coaxial concord with the light receiving part 26 as described above and chemical light emission of the sample was sequentially measured.

For comparison, the same measurement as above was performed using a device which shielded the entire device as shown in FIG. 11 (Comparative Example 1) and partly shielded the gap as shown in FIG. 12 (Comparative Example 2). The results are shown in Table 3.

TABLE 3

|  | Exp. Ex. | Comparative Exs. | |
|---|---|---|---|
|  | 2 | 1 | 2 |
| Signal (count/sec) | 45700 | 43800 | 35300 |
| Noise (count/sec) | 29 | 270 | 35 |
| Signal/Noise | 1570 | 162 | 1010 |
| Measurement time (sec/sample) | 2 | 2 | 2 |

(The unit for Signal and Noise is cps.)

According to the light measurement device of the present invention, invasion of an outside light or a stray light from the samples other than the measurement target sample can be effectively prevented by forming a simple light-shielding structure shielding the light receiving part of the light detection part by a shutter when light measurement is not underway, and by a light-shielding member when light measurement is underway. Since invasion of an outside light into the light detection part can be prevented, degradation of emitted light detection element by invaded outside light can be avoided. When light is measured, the gap between the light receiving part of the light detection part and the reaction vessel can be sufficiently shielded and occurrence of noise preventing the determination can be eliminated.

As described above, the present invention is advantageous in that invasion of an outside light or a stray light into the light path through the light receiving part during measurement or non-measurement can be effectively prevented and degradation of emitted light detection element or measurement noise can be eliminated. In addition, the reaction vessel can be accurately set, thereby greatly improving the measurement precision.

Further, since a light-shielding case is not necessary, the apparatus can be made small and the production cost can be reduced.

According to this measurement apparatus, a microplate having a plurality of hole-like openings can be used as a reaction vessel, which is mounted on a transfer means to enable sequential measurement of a sample contained in each vessel, thus resulting in improved measurement efficiency.

The method for assaying the nucleic acid in a sample comprises the use of an automated apparatus for assaying a DNA probe having the structure as described.

Figure 16:
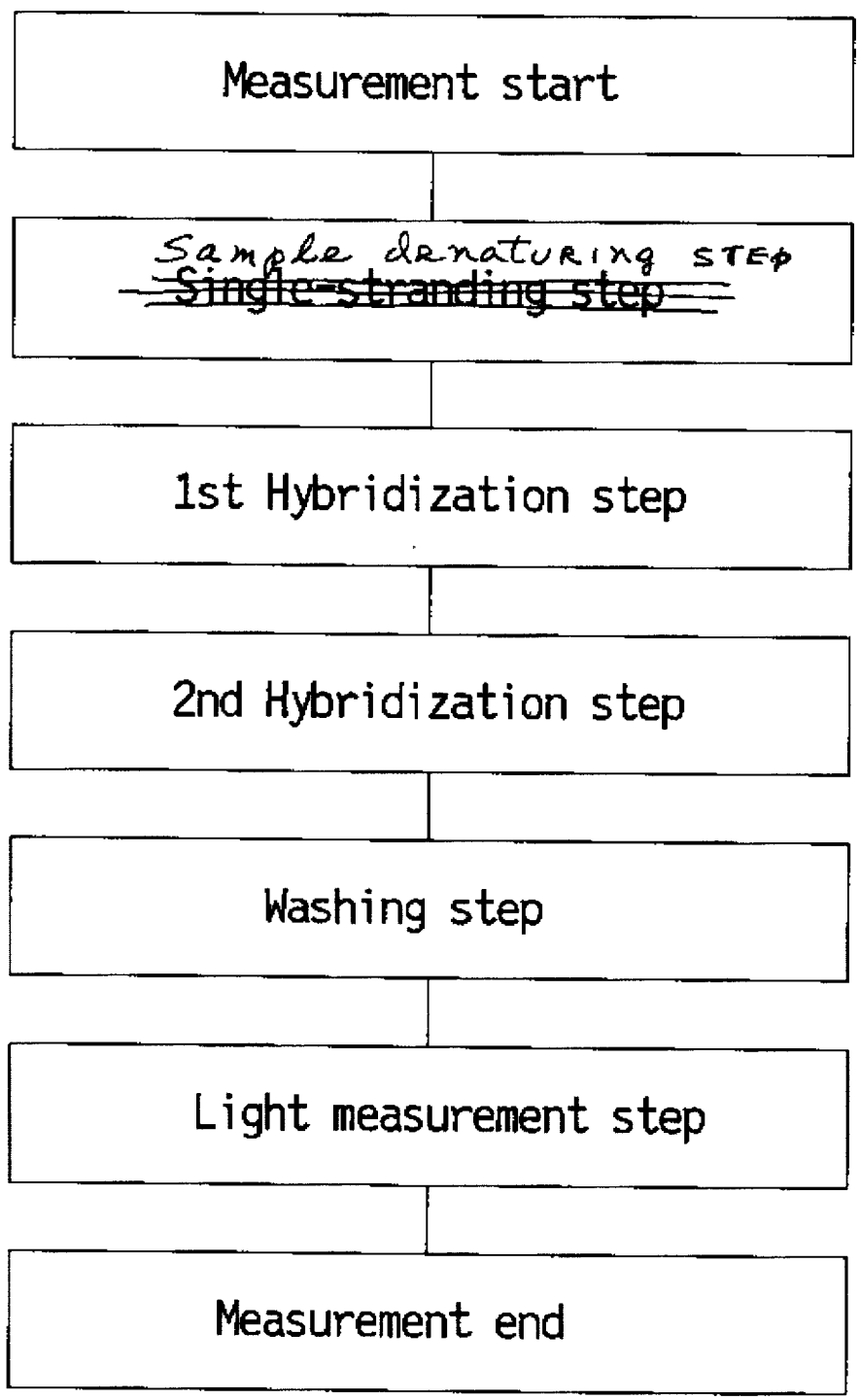
FIG. 16 is a flow chart showing an outline of the measurement steps by the method of the present invention.

The treatment system by hybridization using a DNA probe (which system being the target of the present invention) utilizes hybridization of the nucleic acid in a known sample and a DNA probe. In assaying the nucleic acid in the sample, a minor difference was found between the hybridization methods involving one step and two step (Sandwich method), as well as when involving a DNA sample assay and a RNA sample assay. In the following explanation, however, a typical DNA sample Sandwich hybridization as shown in the flow chart of FIG. 16 was selected. There is no essential difference from the above-mentioned other measurement methods.

In general, a DNA sample Sandwich hybridization method involves the following 5 steps:

(1) A single-stranding step for denaturing a double-stranded DNA in a sample into a single-stranded one with acid, alkali or heat;

(2) A first hybridization step wherein the single-stranded DNA sample is added to a reaction vessel in which a synthetic DNA complementary to the DNA sample has been immobilized onto a solid phase carrier such as a microplate, followed by hybridization at a suitable constant temperature;

(3) A second hybridization step wherein a DNA probe marked with an enzyme is added to said reaction vessel, followed by Sandwich hybridization of the captured DNA sample at a suitable constant temperature as in the first hybridization step;

(4) A washing step wherein a DNA sample which was not captured with the complementary DNA and a marked DNA probe which was not bound with the captured DNA sample are B/F separated from the DNA immobilized on the solid phase carrier by Sandwich hybridization, as in known immunoassay; and (5) A light measurement step that is performed by optically measuring the change occurred in the substrate by catalysis of the enzyme.

In denaturing the sample into a single-stranded one, an arm 6 of the dispense unit B as shown in FIG. 3 is moved downward to set a tip B2, carried in a tip rack B1 shown in FIG. 1, at the head portion of a tip nozzle 7, with selected amounts of an alkaline denaturant in an alkaline denaturant reservoir A2 and a sample contained in the sample tube A1 are sucked and simultaneously injected in a mixing tank 4 in a reagent cassette 1. The mixed solution is thoroughly mixed in the mixing tank 4 several times by repetition of suction and injection with the tip nozzle 7. By this step, the DNA sample is prepared into a single-stranded one.

Meanwhile, a reaction vessel 5, having a bound DNA probe immobilized therein, in accord with the desired measurement item, is housed in the reagent cassette. The reaction vessel 5 is held by a container holding device 12 in said dispense unit B and transported to the holder 16a in the measurement rack 16 in the stocker part 14 in the hybridization unit D.

The hybridization step is performed twice. In the first hybridization step, a sample to be made single-stranded is sucked from the mixing tank 4 in the reagent cassette with the tip nozzle 7 equipped with the tip B4 of the dispense device B and dispensed to the reaction vessel 5 housed in the measurement rack 16 placed at the predetermined position 18 on the dispense line 17 of FIG. 4. Then, the measurement rack 16 is passed through an incubator part 15 by the circulating mechanism of the hybridization unit to subject the reaction vessel 5 to heating by keeping same in a heating atmosphere at about 50° for 15–30 minutes for hybridization in the reaction vessel 5.

In the second hybridization step, a reagent containing a DNA probe, in accord with the selected measurement item, is sucked from the reagent pack 2 in the reagent cassette 1 with the tip nozzle 7 equipped with the aforementioned tip and dispensed to the reaction vessel 5 after the first hybridization, which is placed at the predetermined position 18 on the disperse line 17, whereafter the measurement rack 16 is passed through an incubator part 15 by the circulating device as in the above.

In the one step method, the above-mentioned hybridization step is performed after a single-stranded sample and a marked probe are respectively dispensed to the reaction vessel 5.

In a B/F separation step following the hybridization steps, the content of the reaction vessel 5 is sucked with the discharge nozzle 9 of the dispense unit B and discharged outside, and a washing solution is sucked from the washing solution reservoir A3 of the sample-reagent unit with a washing nozzle 10 and injected into the reaction vessel 5, followed by heating (50° C. for 10 minutes) in the incubator part 15 as in the aforementioned hybridization step. By this step, the B/F separation is done in the reaction vessel 5. After incubation, the washing solution is sucked with the discharge nozzle 9 and discharged outside to remove the free marked probe and the sample remaining in the vessel.

The discharge nozzle 9 is coupled to a diaphragm pump etc. and the washing nozzle 10 is coupled to a pipet capable of sucking and injecting a certain amount of a washing solution.

In the light measurement step, an enzyme substrate is sucked from a reagent pack 2 with the tip nozzle 7 equipped with the tip B2 of the dispense unit B and dispensed to the reaction vessel 5 after the B/F separation. In the same manner as in the above hybridization step, the mixture in the reaction vessel is incubated at the incubator part 15 (37° for 15 minutes) and subjected to the measurement of a light change in the reaction vessel 5 by the light measurement unit F on a transport line 20 in the circulation mechanism.

As described in detail in the foregoing description, the apparatus for automated assay of a DNA probe of the present invention enables automated assay of a nucleic acid in a sample and allows measurement operators to be released from tedious and time-consuming work and error due to inconsistent control of hybridization temperatures by an individual operator and contamination due to a very low concentration of a sample.

According to the method for assaying the nucleic acid in a sample using the above-mentioned apparatus for automated assay of DNA probe, an automated, continuous, high precision measurement of a light change in a sample in a reaction vessel, as well as dependable, highly efficient measurement become attainable.

What is claimed is:

1. An apparatus for an automated assay of a sample using a DNA probe, which is performed by hybridizing a nucleic acid in a sample with a DNA probe marked with an enzyme and optically measuring a change that occurs in a substrate by catalysis of said enzyme which is bound with said probe hybridized with said nucleic acid in said sample to assay said nucleic acid in said sample, comprising:

A—a sample-reagent unit, comprising said sample, reagents, and reaction vessel;

B—a sample-reagent dispense unit in communication with said sample-reagent unit, comprising means to access and deliver said sample and reagents into and out of said reaction vessel;

C—a reaction vessel transport unit in communication with said sample-reagent dispense unit, comprising means for transporting said reaction vessel;

D—a hybridization unit in communication with said reaction vessel transport unit, comprising means for shaking and hybridizing said sample with said DNA probe in said reaction vessel;

E—a B/F separation unit composed of said sample-reagent unit A, said sample-reagent dispense unit B, and said hybridization unit D, the combination of which comprises means to separate unhybridized (F) from hybridized (B) sample nucleic acid that is bound to said reaction vessel; and F—a light measurement unit in communication with said hybridization unit, comprising means to measure the optical change of the contents of said reaction vessel.

2. The apparatus of claim 1, wherein said sample-reagent unit A comprises (1) a sample tube comprising said sample, (2) a reaction vessel in which a capturing DNA probe has been immobilized, (3) a reagent pack comprising said DNA probe marked with said enzyme and a substrate, (4) a reagent cassette composed of a mixing tank and a holder in which said reaction vessel is movably held, (5) an alkaline denaturant reservoir, and (6) a washing solution reservoir.

3. The apparatus of claim 2, wherein said sample-reagent dispense unit B comprises (1) a freely movable arm, wherein said arm moves to the directions of the X-Y-Z axes, (2) means to move said arm, (3) a tip nozzle set in said arm, (4) a tip for said tip nozzle, and (5) a tip rack holding said tip wherein said tip is set at the head portion of said tip nozzle by moving said arm, thereby enabling suction and injection of said sample in said sample tube and said reagent in said reagent pack.

4. The apparatus of claim 3, wherein said reaction vessel transport unit C comprises (1) means for holding a vessel wherein said holding means is formed on said arm, (2) means to move said arm, and (3) means to transport said reaction vessel, wherein said reaction vessel is carried by said holding means to a stock part of a measurement rack.

5. The apparatus of claim 4, wherein said hybridization unit D comprises (1) means to transport said measurement rack from said stock part to an incubator and then back to said stock part, wherein said measurement rack carries reaction vessels, said incubator includes a heating means and a shaking means, and (2) means for sequentially sucking said sample from said sample-reagent dispense unit B and said DNA probe and respectively dispensing same into a reaction vessel located in said measurement rack.

6. The apparatus of claim 5, wherein said B/F separation unit E comprises (1) a discharge nozzle and a washing solution nozzle set in said arm, (2) means for sucking the content of said reaction vessel in said discharge nozzle and for sucking said washing solution from said washing solution reservoir with said washing solution nozzle and injecting said solution into said reaction vessel, and (3) said transport means of said hybridization unit, wherein said content of said reaction vessel is discharged outside said reaction vessel and said washing solution is injected into said reaction vessel.

7. The apparatus of claim 6, wherein said light measurement unit F comprises (1) means for sucking and injecting said substrate from said reagent pack into said reaction vessel after B/F separation, (2) said transport means, and (3) means for measuring an optical change in said reaction vessel.

8. The apparatus of claim 7, wherein said optical measuring means comprises (1) an emitted light detection part having a light receiving part at the head portion thereof, (2) a hollow light-shielding member movable along the peripheral surface of said light receiving part and said reaction vessel comprising (3) a sample and disposed with its opening in opposite relation to said head portion, wherein said hollow light-shielding member moves to cover a gap formed by said head portion and an upper end of said reaction vessel during said optical measurement.

9. The apparatus of claim 7, wherein said optical measuring means comprises (1) an emitted light detection part, (2) a tubular light receiving part to introduce a light emitted by said sample to said emitted light detection part, (3) a hollow light-shielding member movable along the peripheral surface of said tubular light receiving part, (4) a movable shutter that opens a light path through said tubular light receiving party only when an emitted light measurement is underway, and (5) said reaction vessel further comprising a sample and disposed with its opening in opposite relation to said tubular light receiving part.

10. The apparatus of claim 9, wherein said emitted light detection part comprises (1) a means for photoelectric transfer of said emitted light and (2) a means for determining an emission amount from said photoelectric transfer value.

11. A method for assaying a nucleic acid in a sample by the apparatus of claim 1, comprising the following four steps:

1. a sample denaturing step wherein,
   (a) a sample in a sample tube and an alkaline denaturant from an alkaline denaturant reservoir are sequentially sucked with a tip nozzle equipped with a tip of the sample-reagent dispense unit, simultaneously dispensed to a mixing tank in a reagent cassette and mixed to make the nucleic acid in the sample single-stranded;

2. a hybridization step wherein,
   (a) a reaction vessel, in which a capturing probe has been immobilized, is transported from a reagent cassette into a holder in a measurement rack in a stock part of a hybridization unit by means of a reaction vessel transport unit, and
   (b) the single-stranded nucleic acid of step 1(a) and a DNA probe marked with an enzyme, which was sucked from the reagent pack in the reagent cassette with a tip nozzle equipped with a tip, are dispensed to said reaction vessel, and the measurement rack is passed to an incubator part by a circulation mechanism, wherein said incubator part includes heating and shaking means to allow hybridization in said reaction vessel;

3. a B/F separation and washing step wherein,
   (a) the content of the reaction vessel after the hybridization is sucked with a discharge nozzle of the sample-reagent dispense unit and discharged, a washing solution is sucked from a washing solution reservoir with a washing solution nozzle of said dispense unit and injected into said reaction vessel, the measurement rack is passed to an incubator part by a circulation mechanism, wherein said measurement rack is heated and shaken to allow B/F separation in said reaction vessel, and
   (b) the washing solution is sucked with the discharge nozzle from the reaction vessel after the B/F separation and discharged; and 4. a light measurement step wherein,
   (a) an enzyme substrate is sucked from a reagent pack in the reagent cassette with a tip nozzle equipped with a tip of the sample-reagent dispense unit and injected into the reaction vessel, the measurement rack is passed to an incubator part by a circulation mechanism, wherein said measurement rack is heated, and
   (b) the measurement rack is transported to a light measurement part by the circulation mechanism, wherein said light measurement part measures light change in the reaction vessel by means of a light measurement device.

12. A method for determining a nucleic acid in a sample by the apparatus of claim 1, comprising the following four steps:

1. a sample denaturing step wherein,
   (a) a sample in a sample tube and an alkaline denaturant from an alkaline denaturant reservoir are sequentially sucked with a tip nozzle equipped with a tip of a sample-reagent dispense unit, and simultaneously dispensed to a mixing tank in a reagent cassette and mixed to make the nucleic acid in the sample single-stranded;

2. a hybridization step wherein,
   (a) a reaction vessel, in which a capturing probe has been immobilized, is transported from a reagent cassette into a holder in a measurement rack in a stock part of a hybridization unit by means of a reaction vessel transport unit,
   (b) the single-stranded nucleic acid of step 1(a) is dispensed to said reaction vessel and the measurement rack is passed to the incubator part by a circulation mechanism, wherein said incubator part includes heating and shaking means to allow hybridization in the reaction vessel, and
   (c) a DNA probe marked with an enzyme, which was sucked from the reagent pack in the reagent cassette with a tip nozzle equipped with a tip of the dispense unit, is injected into said reaction vessel, and the measurement rack is passed through an incubator part by a circulation mechanism, wherein hybridization is allowed in said reaction vessel;

3. a B/F separation and washing step wherein,
   (a) the content of the reaction vessel after the hybridization is sucked with a discharge nozzle of the sample-reagent dispense unit and discharged, a washing solution is sucked from a washing solution reservoir with a washing solution nozzle of said dispense unit and injected into said reaction vessel, the measurement rack is passed to an incubator part by a circulation mechanism, wherein said measurement rack is heated and shaken to allow B/F separation in said reaction vessel, and
   (b) the washing solution is sucked for discharge from the reaction vessel after the B/F separation with the discharge nozzle; and 4. a light measurement step wherein,
   (a) an enzyme substrate is sucked from a reagent pack in the reagent cassette with a tip nozzle equipped with a tip of the sample-reagent dispense unit and injected into the reaction vessel, the measurement rack is passed to an incubator part by a circulation mechanism of the hybridization, wherein said measurement rack is heated, and
   (b) the measurement rack is transported to a light measurement part by the circulation device, wherein said light measurement part measures light change in the reaction vessel by means of a light measurement device.

* * * * *